(12) United States Patent
Virtanen

(10) Patent No.: US 6,446,626 B1
(45) Date of Patent: *Sep. 10, 2002

(54) INHALATION DEVICE

(75) Inventor: Risto Virtanen, Nurmijärvi (FI)

(73) Assignee: Astra Aktiebolag, Sodertälje (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,388

(22) PCT Filed: Mar. 13, 1998

(86) PCT No.: PCT/SE98/00463

§ 371 (c)(1),
(2), (4) Date: May 8, 1998

(87) PCT Pub. No.: WO98/41262

PCT Pub. Date: Sep. 24, 1998

(30) Foreign Application Priority Data

Mar. 14, 1997 (SE) .............................. 9700948

(51) Int. Cl.⁷ ............................................. A61M 11/00
(52) U.S. Cl. ............................. 128/200.14; 128/203.15
(58) Field of Search ........................ 128/200.14, 203.15

(56) References Cited

U.S. PATENT DOCUMENTS

| 443,545 | A | * | 12/1890 | Rowland | ............... 128/203.15 |
|---|---|---|---|---|---|
| 2,966,909 | A | * | 1/1961 | Halperin | ................. 128/203.21 |
| 5,331,953 | A | * | 7/1994 | Andersson et al. | ..... 128/203.15 |
| 5,351,683 | A | * | 10/1994 | Chiesi et al. | ........... 128/203.15 |
| 2,705,007 | A | * | 3/1995 | Gerber | ................... 128/203.21 |
| 5,740,792 | A | * | 4/1998 | Ashley et al. | .......... 128/203.15 |

FOREIGN PATENT DOCUMENTS

| GB | 2267484 | 12/1995 |
|---|---|---|
| WO | WO95/07724 | 3/1995 |
| WO | WO/95/29723 | 11/1995 |

* cited by examiner

*Primary Examiner*—Aaron J. Lewis
(74) *Attorney, Agent, or Firm*—Fish & Richardson P.C.

(57) ABSTRACT

An inhaler for administering powder by inhalation and a method of constructing the same, the inhaler comprising: a housing having a screw thread (28) and a substantially circular sealing surface (40) coaxial therewith; a mouthpiece (2) attached to the housing; and a cap (14) for covering at least the mouthpiece (2), the cap (14) having a screw thread (17) for engaging the screw thread (28) on the housing and a substantially circular sealing surface (15) for engaging the sealing surface (40) on the housing; wherein the sealing surfaces (15, 40) are shaped and dimensioned such that the radial force therebetween is substantially constant for any relative position where the sealing surfaces (15, 40) engage one another.

16 Claims, 4 Drawing Sheets

INHALATION DEVICE

The present invention relates to a powder inhaler for administering powder by inhalation.

A number of powder inhalers are known which use different systems for introducing a dose of powder into an air stream. Typically, the powder is inhaled into the lungs of a patient in order to treat, for example, asthma.

EP-A-0237507 discloses one such powder inhaler. This inhaler comprises an inhalation channel and a mouthpiece comprising an air chamber and an outlet nozzle, which together define a flow path through which a stream of air is drawn during inhalation by a user. This inhaler further comprises means for introducing powder into the inhalation channel. During inhalation, air is first drawn into and through the inhalation channel so as to pick up powder. The stream of air containing powder is then drawn through the air chamber and out of the outlet nozzle of the mouthpiece.

Powder inhalers are, however, particularly susceptible to the effects of moisture. In order to alleviate problems associated with moisture uptake it has been proposed to include a desiccant, such as silica gel, in the inhaler to absorb any moisture. It has also been proposed to provide the inhaler with a cap which is either screwed or pressed onto the inhaler body so as to close any flow paths between the stored powder and atmosphere.

DE-C-4415462 discloses a powder inhaler comprising a housing and a cap which is a screw fit to the housing. The cap includes a sealing collar which sealingly engages the inner surface of the neck of the housing when screwed thereto.

In powder inhalers of the kind as disclosed in EP-A-0237507 which comprise an inhaler body and a grip portion at one end thereof, which grip portion is rotatable relative to the inhaler body so as to provide a dose of powder for inhalation, it has been proposed to provide a chamber in the grip portion for containing desiccant and to provide a cap which covers substantially all of the inhaler body and is screwed onto the grip portion so as to seal therewith and thereby exclude moisture from the inhaler body in which the powder is stored.

FIGS. 1 to 3 illustrate such a powder inhaler. The inhaler comprises a mouthpiece 2 comprising an outlet nozzle 4, an inhaler body 6 and a rotatable grip portion 8 for operating a dosing mechanism for providing doses of powder for inhalation. The inhaler body 6 is provided with an opening 10 which is filled with a window 12 through which an indicating wheel (not illustrated) is visible so as to provide an indication as to the usage of the inhaler. The inhaler further comprises a cap 14 comprising a tubular section having a closed end which is configured to fit over the mouthpiece 2 and the inhaler body 6. The cap 14 includes a sealing surface 15 at the inner peripheral edge of the lip 16 at the open end thereof, which sealing surface 13 tapers outwardly in the direction from the closed to the open end of the cap 14. The cap 14 further includes screw threads 17 provided to the inner surface thereof.

The grip portion 8 comprises first and second hollow parts 18, 20 which are mutually configured so as to define an enclosed chamber 22 for containing desiccant when fitted together.

The first part 18 comprises a tubular section 24, in this inhaler of generally cylindrical cross-section, having a circumferential ridge 26 disposed about the outer surface of one, the upper, end thereof to which the inhaler body 6 is clipped and screw threads 28 to which the cap 14 having corresponding screw threads 17 is screwed so as to cover the mouthpiece 2 and the inhaler body 6 and thus form a tight seal. The first part 18 further comprises an upwardly-directed resiliently-biased arm 30 disposed at the periphery of the upper end thereof, which arm 30, on rotation of the grip portion 8, engages part of the dosing mechanism so as to provide a dose of powder for inhalation. The first part 18 yet further comprises a transverse wall 32 which is permeable to moisture. The wall 32 is preferably formed at least in part of cardboard.

The second part 20 comprises a tubular section 34, in this inhaler of generally cylindrical cross-section, one, the lower, end of which is closed by a wall 36. The outer surface of the tubular section 34 includes a plurality of axially-directed ridges 38 which are gripped by a user on rotation of the grip portion 8 and a sealing surface 40 at the outer peripheral edge of the lip 41 at the open end thereof, which sealing surface 40 tapers inwardly in the direction from the closed to the open end of the second part 20. In another inhaler the axially-directed ridges 38 could be replaced by a knurled surface. In this inhaler the inner dimension of the tubular section 34 is configured so as to be a close radial fit over the tubular section 24 of the first part 18.

In use, the cap 14 is first removed by unscrewing in one sense, in this inhaler in the counter-clockwise sense when viewed from above. The grip portion 8 is then rotated in one sense, in this inhaler also in the counter-clockwise sense when viewed from above, through a predetermined angle relative to the inhaler body 6 and back in the opposite, clockwise, sense to the original position. This action operates the dosing mechanism to provide a dose of powder for inhalation. The user then takes the mouthpiece 2 in the lips and inhales so as to draw powder into the lungs. After use, the cap 14 is then replaced by screwing on in the other, clockwise, sense when viewed from above. In screwing on the cap 14 the sealing surface 15 on the cap 14 is brought into engagement with the sealing surface 40 on the grip portion 8, with a right seal being achieved by screwing the cap 14 tightly to the grip portion 8.

Whilst acceptable, there are a number of drawbacks associated with this sealing arrangement. Firstly, if the cap 14 is not screwed onto the grip portion 8 tightly enough, a proper seal will not be made and there will be a risk that the cap 14 will work loose and fall off. Conversely, if the cap 14 is screwed too tightly onto the grip portion 8, a user may find the cap 14 difficult to remove. Indeed, where the cap 14 is screwed too tightly onto the grip portion 8, it is possible that the lip 16 on the cap 14 or even the lip 41 on the grip portion 8 may be damaged. This is particularly the case where the inhaler is assembled by machine as it is likely that the machine may overtighten the cap 14.

It is thus an aim of the present invention to provide an inhaler in which the seal with the cap is achieved without the cap having to be screwed overly tightly.

Accordingly, the present invention provides an inhaler for administering powder by inhalation, comprising: a housing having a screw thread and a substantially circular sealing surface coaxial therewith; a mouthpiece attached to the housing; and a cap for covering at least the mouthpiece, the cap having a screw thread for engaging the screw thread on the housing and a substantially circular scaling surface for engaging the scaling surface on the housing; wherein the sealing surfaces are shaped and dimensioned such that the radial force therebetween is substantially constant for any relative position where the sealing surfaces engage one another; characterized in that the housing comprises a body and a grip portion which is rotatable relative to the body and on rotation provides a dose of powder for inhalation, in that the screw thread and the sealing surface on the housing are provided on the grip portion and in that the sealing surface on the grip portion is disposed axially forward, in the direction of fitting the cap to the housing, of the screw thread on the grip portion.

Preferably, the sealing surface on the grip portion comprises a substantially cylindrical outwardly-facing surface.

Preferably, the sealing surface on the cap comprises a substantially cylindrical inwardly-facing surface.

Preferably, the sealing surface on the grip portion is provided by a circular lip.

Preferably, the sealing surface on the cap is provided by a circular lip.

More preferably, the forward end, in the direction of fitting the cap to the housing, of at least one of the lip defining the sealing surface on the grip portion and the lip defining the sealing surface on the cap is shaped so as to guide the sealing surface on the cap onto the sealing surface on the grip portion.

In one embodiment the respective forward end is rounded.

In another embodiment the respective forward end is tapered.

Preferably, at least one of the lip defining the sealing surface on the grip portion and the lip defining the sealing surface on the cap is resiliently displaceable.

More preferably, at least one of the lip defining the sealing surface on the grip portion and the lip defining the sealing surface on the cap is formed of a resilient material.

Still more preferably, in the relaxed state, the internal diameter of the lip defining the sealing surface on the cap is smaller than the external diameter of the lip defining the sealing surface on the grip portion.

Preferably, at least one of the sealing surface on the grip portion and the sealing surface on the cap is a roughened surface.

More preferably, the respective sealing surface has a matt surface finish.

Preferably, the housing and the cap are both substantially cylindrical and the mouthpiece and the grip portion are disposed at opposite ends of the housing.

Preferably, the outer surface of the grip portion has a knurled or ridged surface which can be gripped by a user.

Preferably, the grip portion includes a chamber for containing desiccant and at least a part of the grip portion defining the chamber which faces inwardly is permeable to moisture.

Thus, by virtue of the construction of the inhaler of the present invention the frictional resistance to rotation of the cap is substantially constant irrespective of how fully the cap is screwed onto the housing. In addition, a tight seal is achieved irrespective of the area of contact between the sealing surfaces. In a preferred embodiment the sealing surfaces are configured such that the force required to screw the cap onto the housing is sufficiently high as to prevent the cap from working loose and falling off, but sufficiently low as to enable a user to screw and unscrew the cap with relative ease.

A preferred embodiment of the present invention will now be described hereinbelow by way of example only with reference to the accompanying drawings, in which.

Figure 1:
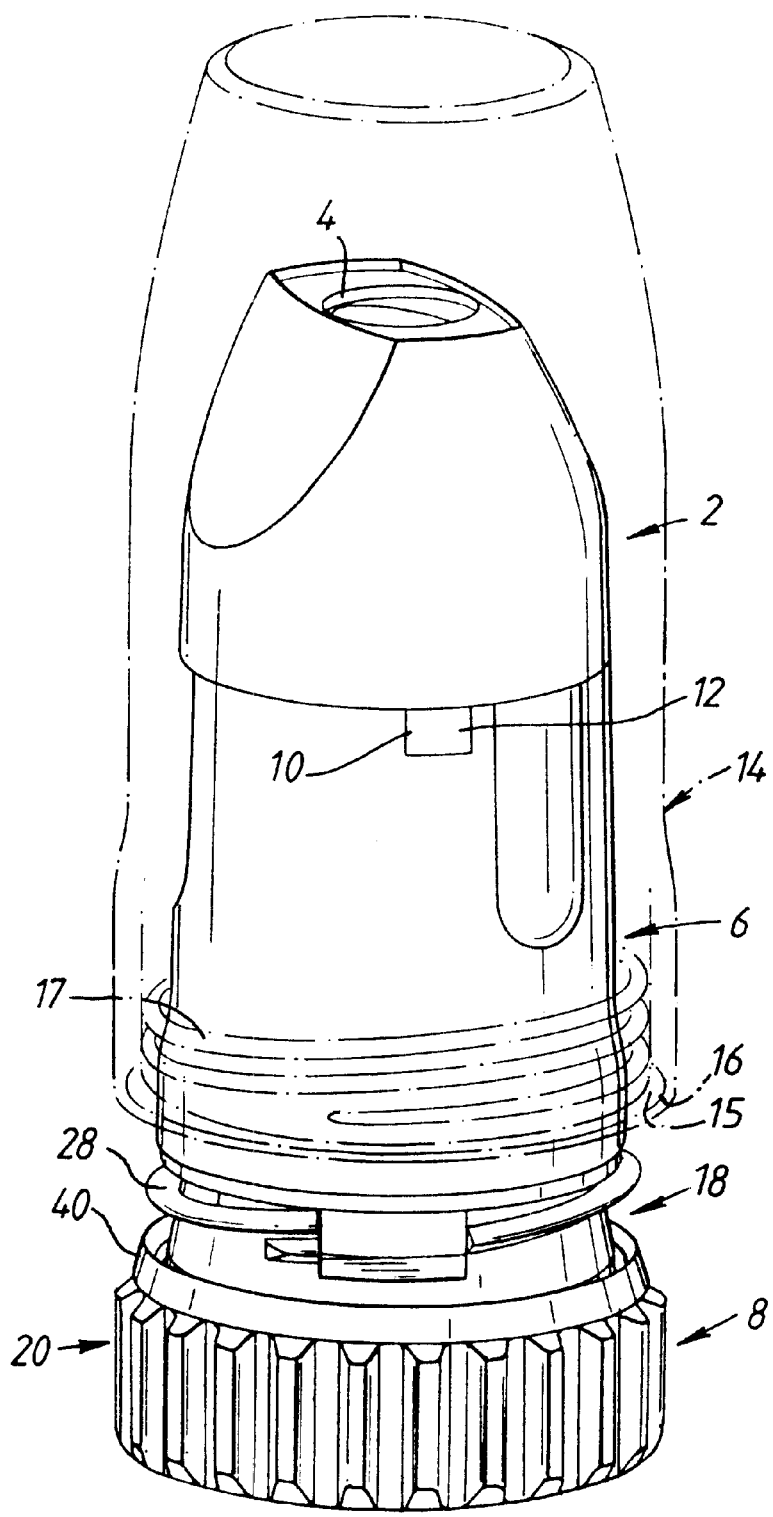
FIG. 1 illustrates a perspective view of a powder inhaler.
Figure 2:
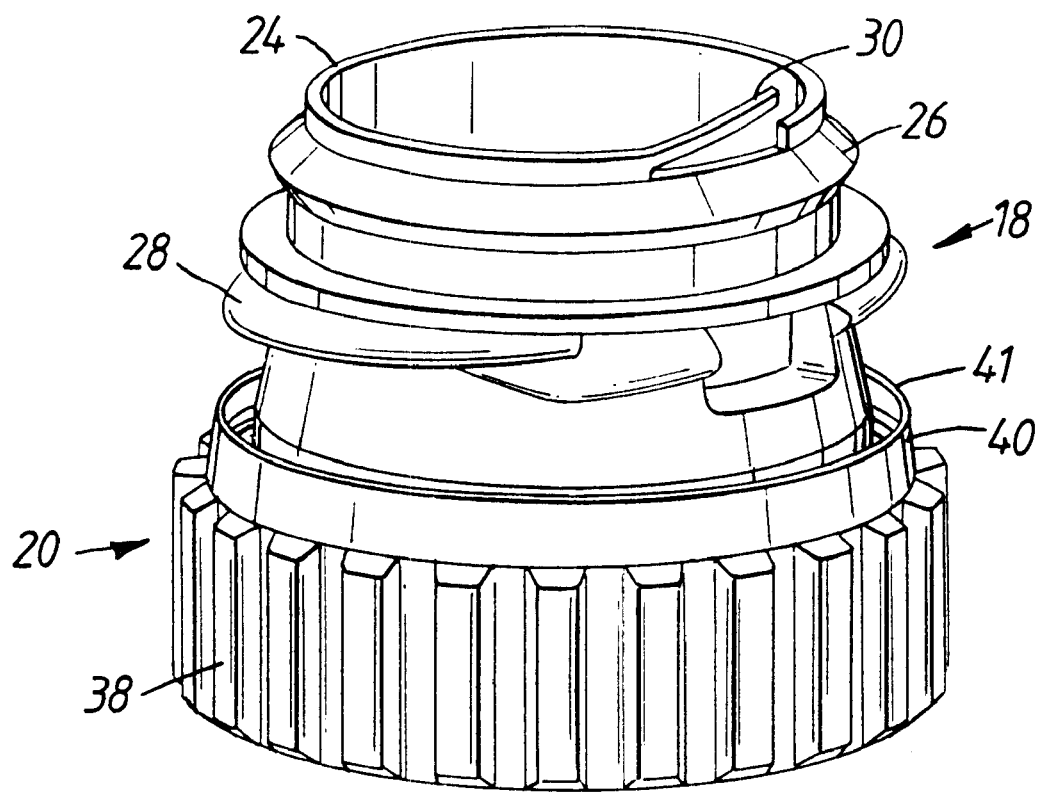
FIG. 2 illustrates the grip portion of the inhaler of FIG. 1.
Figure 3:
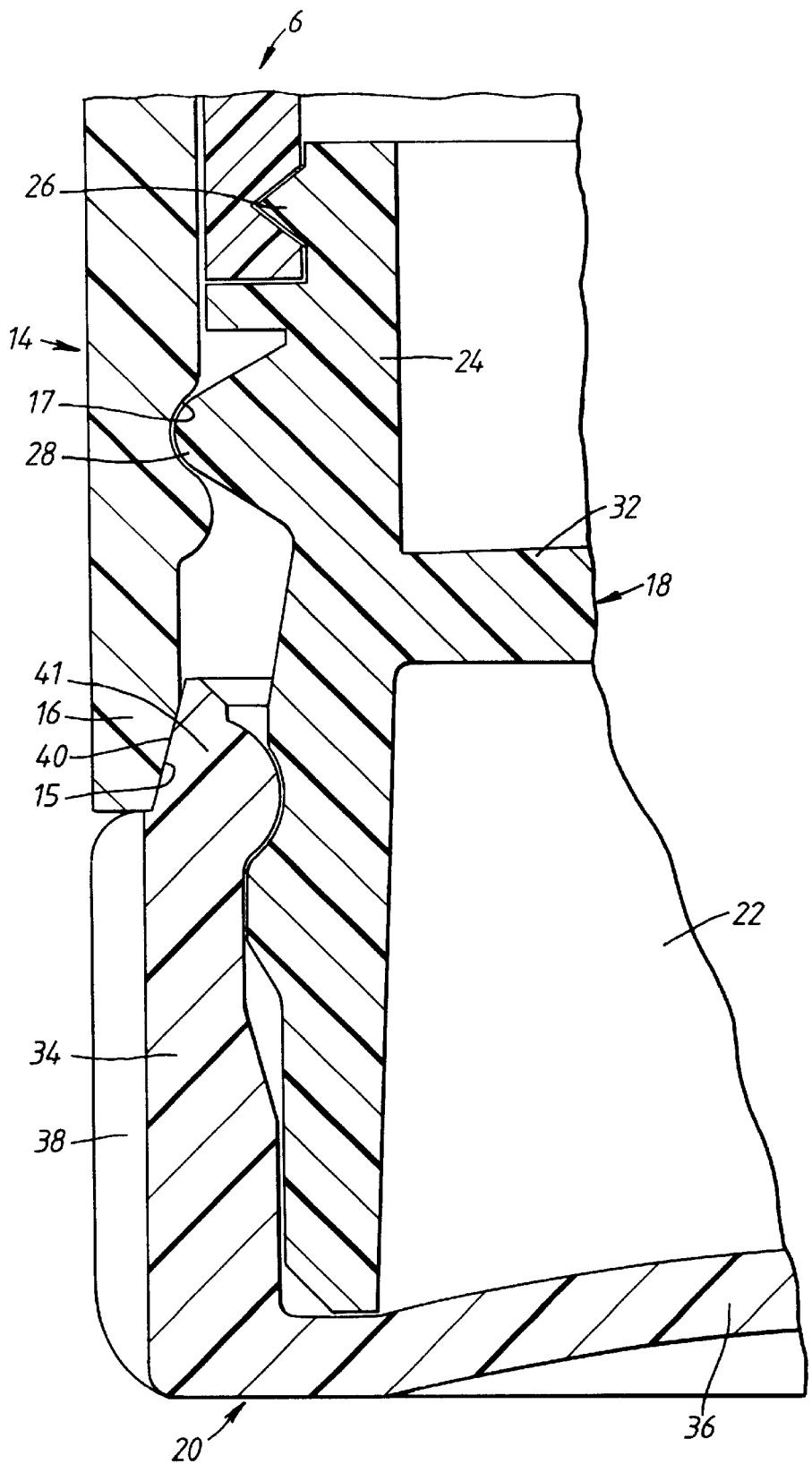
FIG. 3 illustrates a fragmentary vertical sectional view of the inhaler of FIG. 1.

Structurally, the powder inhaler in accordance with the preferred embodiment of the present invention is quite similar to the above-described powder inhaler. For this reason, and in order to avoid unnecessary duplication of description, only the structural differences will be described in detail and reference is made to the preceding description.

This inhaler differs from the above-described powder inhaler principally in that the sealing surface 15 on the cap 14 and the sealing surface 40 on the grip portion 8 comprise axially-extending cylindrical surfaces. In this embodiment the sealing surface 15 on the cap 14 is provided by the inner surface of the circumferential lip 16 at the open end thereof and the sealing surface 40 on the grip portion 8 is provided by the outer surface of the circumferential lip 41 at the open end of the tubular section 34 of the second part 20. With this arrangement, when the cap 14 is screwed onto the grip portion 8, the inwardly-facing sealing surface 15 on the cap 14 engages and seals with the outwardly-facing sealing surface 40 on the grip portion 8. Since both the sealing surface 15 on the cap 14 and the sealing surface 40 on the grip portion 8 are substantially co-axial, when at rest, the force acting therebetween is principally a radial force. Thus, as the cap 14 is screwed onto the grip portion 8, essentially the only resistance that will have to be overcome is that due to friction. It will of course be appreciated that as the area of contact between the sealing surface 15 on the cap 14 and the sealing surface 40 on the grip portion 8 increases, then so will the frictional resistance to rotation. This increase in resistance is, however, relatively insignificant, certainly when compared to the level of resistance encountered in the first-described powder inhaler where the axial force increases significantly as the cap 14 is screwed further onto the grip portion 8.

In this embodiment the outer peripheral edge 41a of the lip 41 defining the sealing surface 40 on the grip portion 8 is rounded and the inner peripheral edge 16a of the lip 16 defining the sealing surface 15 on the cap 14 is tapered outwardly in the direction from the closed to the open end thereof. By so shaping the lip 41 on the grip portion 8 and the lip 16 on the cap 14, the sealing surface 15 defined by the lip 16 is guided onto the sealing surface 40 defined by the lip 41. It will of course be appreciated that the outer peripheral edge 41a of the lip 41 on the grip portion 8 could alternatively be tapered inwardly in the direction from the closed to the open end of the second part 20 thereof and the inner peripheral edge 16a of the lip 16 on the cap 14 could alternatively be rounded. Indeed, the outer peripheral edge 41a of the lip 41 on the grip portion 8 and the inner peripheral edge 16a of the lip 16 on the cap 14 could have any shape which assists in guiding the sealing surface 15 defined by the lip 16 onto the sealing surface 40 defined by the lip 41.

In a preferred embodiment one or both of the lip 16 defining the sealing surface 15 on the cap 14 and the lip 41 defining the sealing surface 40 on the grip portion 8 are formed from a resilient material. In another embodiment one or both of the lip 16 defining the sealing surface 15 on the cap 14 and the lip 41 defining the sealing surface 40 on the grip portion 8 can be formed of a sufficiently small thickness as to be resiliently displaceable. With these arrangements, the internal diameter of the sealing surface 15 defined by the lip 16 on the cap 14 can be smaller than the external diameter of the sealing surface 40 defined by the lip 41 on the grip portion 8; these diameters being those when the sealing surfaces 15, 40 are not acted upon and hence in the non-displaced, relaxed or natural state. Thus, with the cap 14 screwed onto the grip portion 8, one or both of the lip 16 defining the sealing surface 15 on the cap 14 and the lip 41 defining the sealing surface 40 on the grip portion 8 are displaced from the relaxed state so as to provide an increased radial force. In this embodiment the increased radial force will contribute to the frictional force which resists loosening of the cap 14.

Figure 4:
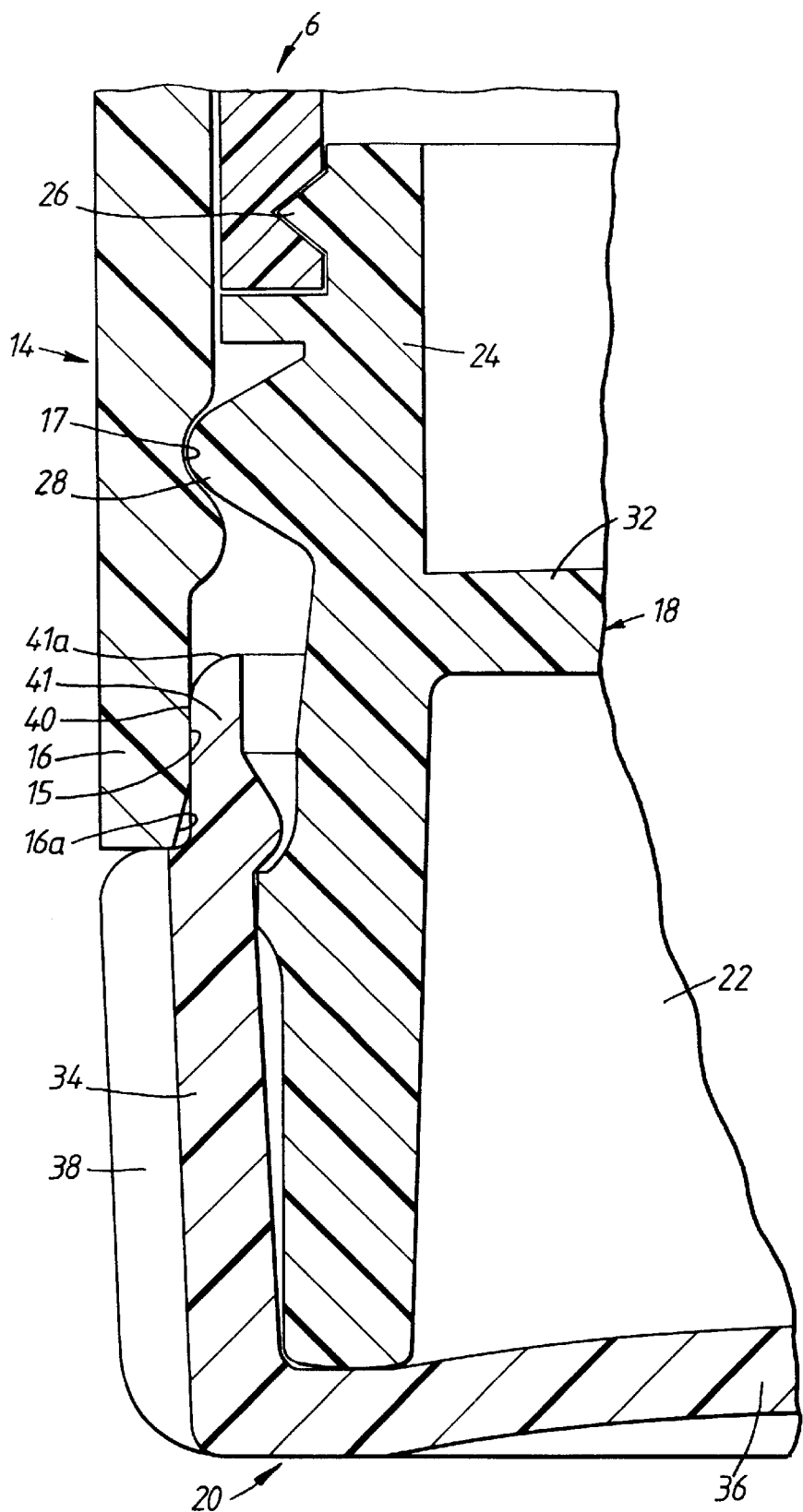
FIG. 4 illustrates a fragmentary vertical sectional view of a powder inhaler in accordance with a preferred embodiment of the present invention.

In this embodiment, as illustrated in FIG. 4, the lip 41 on the second part 20 of the grip portion 8 defining the sealing surface 40 is unsupported from behind. Thus, if formed from a resilient or flexible material, the lip 41 on the grip portion 8 can be deflected radially inwardly. In this way, when the cap 14 is screwed onto the grip portion 8, the lip 41 on the grip portion 8 is deflected and acts to provide a sealing force. This sealing force is relatively constant throughout the travel of the cap 14 in being screwed onto the grip portion 8. This can be contrasted to the arrangement of the first-described powder inhaler where the lip 41 defining the sealing surface 40 on the grip portion 8 is supported and immovable. The first-described powder inhaler relies on compression of the respective lips 16, 41 on the grip portion 8 and the cap 14, neither of which can be made from a particularly resilient material. Thus, in that powder inhaler the resistance to screwing on the cap 14 will increase dramatically as the cap 14 is screwed onto the grip portion 8.

Where the lip 41 defining the sealing surface 40 on the grip portion 8 is formed from a flexible plastics material, typically by moulding, the cap 14 can tend to stick to the sealing surface 40. In a preferred embodiment, in order to alleviate this problem, the sealing surface 40 can be formed with or treated to have a slightly roughened finish. It will of course be appreciated that the sealing surface 40 should not be too rough, since a very rough surface would increase the resistance to screwing on the cap 14. In a preferred embodiment the sealing surface 40 has a matt finish.

Finally, it will be understood by a person skilled in the art that the present invention has been described in its preferred embodiment and can be modified in many different ways without departing from the scope of the invention as defined in the appended claims. For example, one possible modification is to seat an annular ring formed of resilient material, typically rubber, in one of the sealing surfaces 15, 40 such that the annular ring will transmit only a radial force therebetween.

What is claimed is:

1. A powder inhaler for administering powder by inhalation, comprising:
    a housing having a screw thread and a substantially circular sealing surface coaxial therewith, the sealing surface of the housing being separate from the screw thread of the housing;
    a mouthpiece attached to the housing; and
    a cap for covering at least the mouthpiece, the cap having a screw thread for engaging the screw thread on the housing and a substantially circular sealing surface for engaging the sealing surface on the housing, said sealing surfaces opposing each other radially and exerting radially directed sealing force against each other,
    wherein the sealing surfaces are shaped and dimensioned such that said radially directed sealing force therebetween is substantially constant for any relative rotational position where the sealing surfaces engage one another,
    wherein the housing comprises a body and a grip portion which is rotatable relative to the body and on rotation provides a dose of powder for inhalation, and the screw thread and the sealing surface on the housing are provided on the grip portion, and the sealing surface on the grip portion is disposed axially forward, in the direction of fitting the cap to the housing, of the screw thread on the grip portion.

2. The inhaler of claim 1, wherein the sealing surface on the grip portion comprises a substantially cylindrical outwardly-facing surface.

3. The inhaler of claim 2, wherein the sealing surface on the cap comprises a substantially cylindrical inwardly-facing surface.

4. The inhaler of claim 1, wherein the sealing surface on the grip portion is provided by a circular lip.

5. The inhaler of claim 4, wherein the sealing surface on the cap is provided by a circular lip.

6. The inhaler of claim 5, wherein at least one of the lip defining the sealing surface on the grip portion and the lip defining the sealing surface on the cap is resiliently displaceable.

7. The inhaler of claim 6, wherein, in a relaxed state, the internal diameter of the lip defining the sealing surface on the cap is smaller than the external diameter of the lip defining the sealing surface on the grip portion.

8. The inhaler of claim 5, wherein at least one of the lip defining the sealing surface on the grip portion and the lip defining the sealing surface on the cap is formed of a resilient material.

9. The inhaler of claim 5, wherein a forward end, in the direction of fitting the cap to the housing, of at least one of the lip defining the sealing surface on the grip portion and the lip defining the sealing surface on the cap is shaped so as to guide the sealing surface on the cap onto the sealing surface on the grip portion.

10. The inhaler of claim 9, wherein the forward end of the sealing surface shaped to guide the sealing surface on the cap onto the sealing surface on the grip portion is tapered.

11. The inhaler of claim 9, wherein the forward end of the sealing surface shaped to guide the sealing surface on the cap onto the sealing surface on the grip portion is rounded.

12. The inhaler of claim 1, wherein at least one of the sealing surface on the grip portion and the sealing surface on the cap comprises a roughened surface.

13. The inhaler of claim 12, wherein the sealing surface comprising a roughened surface comprises a matt finish.

14. The inhaler of claim 1, wherein the housing and the cap are both substantially cylindrical and the mouthpiece and the grip portion are disposed at opposite ends of the housing.

15. The inhaler of claim 1, wherein the outer surface of the grip portion has a knurled or ridged surface which can be gripped by a user.

16. The inhaler of claim 1, wherein the grip portion includes a chamber for containing desiccant and at least a part of the grip portion defining the chamber which faces inwardly is permeable to moisture.

* * * * *